(12) United States Patent
Francis

(10) Patent No.: US 8,021,322 B1
(45) Date of Patent: Sep. 20, 2011

(54) ENTERAL FEEDING APPARATUS

(76) Inventor: Nathania A. Francis, Smithtown, NY (US)

(*) Notice: Subject to any disclaimer, the term of this patent is extended or adjusted under 35 U.S.C. 154(b) by 0 days.

(21) Appl. No.: 12/955,534

(22) Filed: Nov. 29, 2010

(51) Int. Cl.
*A61M 31/00* (2006.01)
*A61B 5/00* (2006.01)

(52) U.S. Cl. ............ 604/66; 604/131; 600/300; 600/301

(58) Field of Classification Search .............. 604/65–67, 604/131; 600/300–301
See application file for complete search history.

(56) References Cited

U.S. PATENT DOCUMENTS

| | | | |
|---|---|---|---|
| 5,368,562 A * | 11/1994 | Blomquist et al. | 604/65 |
| 5,658,250 A | 8/1997 | Blomquist et al. | |
| 5,681,285 A * | 10/1997 | Ford et al. | 604/151 |
| 5,685,844 A * | 11/1997 | Marttila | 604/65 |
| 5,788,669 A | 8/1998 | Peterson | |
| 5,951,510 A | 9/1999 | Barak | |
| 6,024,539 A | 2/2000 | Blomquist | |
| 6,241,704 B1 | 6/2001 | Peterson et al. | |
| 7,347,836 B2 | 3/2008 | Peterson et al. | |
| 7,454,314 B2 | 11/2008 | Holland et al. | |
| 2002/0029776 A1 | 3/2002 | Blomquist | |
| 2005/0177395 A1 | 8/2005 | Blomquist | |
| 2005/0215948 A1 | 9/2005 | Adams | |
| 2006/0106649 A1 | 5/2006 | Eggers et al. | |
| 2006/0122867 A1 | 6/2006 | Eggers et al. | |
| 2006/0136271 A1 | 6/2006 | Eggers et al. | |
| 2006/0143051 A1 | 6/2006 | Eggers et al. | |
| 2007/0161870 A1 * | 7/2007 | Abel | 600/300 |
| 2007/0207554 A1 * | 9/2007 | Lin et al. | 436/514 |
| 2008/0071210 A1 | 3/2008 | Moubayed et al. | |
| 2008/0167607 A1 | 7/2008 | Pfeiffer et al. | |
| 2008/0195047 A1 | 8/2008 | Price | |
| 2008/0219928 A1 * | 9/2008 | Becker et al. | 424/9.1 |
| 2008/0306353 A1 * | 12/2008 | Douglas et al. | 600/301 |
| 2009/0036753 A1 * | 2/2009 | King | 600/301 |
| 2009/0270810 A1 | 10/2009 | DeBelser et al. | |
| 2010/0100037 A1 | 4/2010 | Cozmi et al. | |

OTHER PUBLICATIONS

Marik, Paul E. MD and Zaloga, Gary P. MD, FCCM; "Early Enteral Nutrition in Acutely III Patients: A Systematic Review," Critical Care Medicine; Abstract 2 pages; vol. 29, Issue 12 (Dec. 2001).
Flexiflo Quantum Enteral Pump, Operating Manual, Abbott Laboratories, 1997, 2005, 2007, 2009, 24 pages.
KANGROO ePump Enteral Feeding Pump, Kendall, Tyco Healthcare Group, LP, 44 pages, 2007.
Compat Enteral Delivery System, Operating Instructions for Model No. 9522041/199245, Nestle Nutrition, 44 pages.
Compat Enteral Delivery System, Operating Instructions for Model No. 9517455/199235, Nestle Nutrition, 40 pages.

* cited by examiner

*Primary Examiner* — Nicholas D Lucchesi
*Assistant Examiner* — Quynh-Nhu H Vu
(74) *Attorney, Agent, or Firm* — Hoffmann & Baron, LLP

(57) ABSTRACT

Embodiments of the present invention include a enteral feeding apparatus and/or system in which an enteral feeding pump can be configured to deliver enteral formula to a patient in accordance with a delivery parameter determined using patient information associated with a patient to be treated and formula information associated with an enteral formula to be delivered to the patient. Exemplary embodiments can determine an estimated daily caloric intake for a patient and can configure the enteral feeding pump to satisfy the caloric requirements of the patient. Exemplary embodiments are also able to monitor the delivery of the enteral formula to ensure that the patient is being properly treated.

27 Claims, 9 Drawing Sheets

|  |  |  | 610 |
|---|---|---|---|
| Patient Sex (choose one) | Male | Female | |
| Height (Cm/Inches) | | | |
| Admission weight (lbs/kg) | | | |
| BMI | | | |
| BSA m2 | | | |
| Select: Unit department or desired ( kcal/kg ) | | | |

Rows BMI through Select are braced as 620.

Calculate Caloric Requirement ← 615    620

| Ideal Body Weight (IBW) | |
|---|---|
| Adjusted Body Weight (ADW) | |
| Calculation Weight | |
| Estimated Caloric Requirement (25-30 Kcal/kg/day) | |

625

| Estimated Nutrition formula (cal/ml) | Estimated Target Rate (ml/hour) | Calories Delivered (kcal/day) | Protein Delivered (g/day) (optional) |
|---|---|---|---|
| Glucerna 1.2 | 40 | 1152 | 57 |
| Jevity 1.2 | 40 | 1152 | 53 |
| Nepro 1.8 | 25 | 1080 | 48 |
| Optimental 1.5 | 30 | 1080 | 55 |
| Oxepa 1.5 | 30 | 1080 | 45 |
| Perative 1.3 | 35 | 1092 | 56 |
| Two Cal HN 2.0 | 25 | 1200 | 50 |

630    632    Figure 6    634    636

| Date/Time | Enteral Formula | Rate | Total Volume Administered | Total Caloric Intake | Caloric Requirement | Compensatory Enteral calories | Total Caloric Deficit |
|---|---|---|---|---|---|---|---|
| 08/10/10 13:00 | Jevity | 70 | 1800 | 2160 | 2160 | 0 | 0 |
| 08/11/10 14:00 | Jevity | 70 | 960 | 1152 | 2160 | 0 | -1008 |
| 08/12/10 15:00 | Jevity | 70 | 2760 | 2160 | 2160 | 1008 | 0 |
| 08/13/10 16:00 | Jevity | 70 | 1800 | 2160 | 2160 | 0 | 0 |
| 08/14/10 17:00 | Nepro | 50 | 1200 | 2160 | 2160 | 0 | 0 |
| 08/15/10 18:00 | Nepro | 50 | 1000 | 1800 | 2160 | 0 | -360 |
| 08/16/10 19:00 | Nepro | 50 | 1400 | 2520 | 2160 | 360 | 0 |
| 08/17/10 20:00 | Nepro | 50 | 1200 | 2160 | 2160 | 0 | 0 |
| 08/18/10 21:00 | Oxepa | 60 | 1440 | 2160 | 2160 | 0 | 0 |
| 08/19/10 22:00 | Jevity | 70 | 1000 | 1200 | 2160 | 0 | -960 |
| 08/20/10 23:00 | Jevity | 70 | 1800 | 2160 | 2160 | 0 | 0 |

Figure 9

ENTERAL FEEDING APPARATUS

BACKGROUND

Embodiments of the present invention relate to the art of enterally feeding, and, in particular, concern the ability to enhance the control of delivery responsive to patients needs.

Patients that are unable to take food or medications due to the inability to swallow typically receive nutrition intravenously through a catheter, which is referred to as parenteral nutrition, or through a feeding tube, which is referred to as enteral nutrition. Enteral feeding is typically used to feed patients when there is no contraindication of the gastrointestinal tract present. In critical care areas, and for long term use, enteral feeding is advantageous and the preferred method of feeding because it provides nutrition and preserves the intestinal mucous membrane.

While delivery of nutrition enterally is useful and beneficial to patients, its effectiveness can be dependent on proper ordering, administration and monitoring of the enteral feeding. The administration of enteral nutrition is a multidisciplinary process that can be hindered due to breaks in communication, complexities of modern healthcare, and decreasing staff both at the bedside and at the nutritional support level. Risk of complications associated with the enteral delivery of food, increases as a result of gaps in communication.

Enterally feeding can be implemented using enteral feeding pumps that generally deliver a specified volume of formula to the patient at a rate selected by the user. For example, a healthcare provider can set an enteral feeding pump to deliver a prescribed volume of feeding formula at a prescribed rate. Once the pump is set, the pump delivers the feeding formula to the patient at the selected rate. A single enteral feeding pump can be a shared resource for use by a group of patients in a hospital. Each patient can have distinct enteral feeding requirements. If a feeding pump is utilized for different patients and is not properly re-programmed based on the enteral feeding requirements of the patient being fed, the patient can be at risk for improper feeding, which is highly undesirable.

Despite the attention given by healthcare providers to the management and practice of providing adequate nutrition to patients, the patients may be malnourished. For example, factors impeding the daily delivery of enteral nutrition, such as interruptions of enteral feeding to change a patient's body position or other prescribed orders, can result in underfeeding of patients.

SUMMARY

The present invention is, in one aspect, an enteral feeding apparatus that includes an enteral feeding pump and a controller. The enteral feeding pump delivers enteral feeding formula to a patient and the controller controls delivery of the enteral feeding formula based on a delivery parameter determined using a relationship between a patient parameter associated with the patient and a caloric parameter associated with the enteral feeding formula.

In some embodiments, the patient parameter can be an estimated daily caloric intake requirement for the patient, the caloric parameter can be a quantity of calories per a specified volume of the enteral feeding formula, and/or the delivery parameter can be a delivery rate of the enteral feeding formula. The daily estimated caloric intake requirement for the patient can be calculated by the controller based on patient information associated with the patient. In some embodiments, the estimated daily caloric intake requirement is calculated using at least one of the Weir equation, an indirect calorimetry respiratory quotient formula, the Harris Benedict equation, an ideal bodyweight equation, the Devine formula equation, an adjusted body weight equation, and the like. The delivery rate can be determined by generating a quotient of the estimated daily caloric intake requirement divided by the quantity of calories per specified volume and dividing the quotient by a time period over which the enteral formula is to be delivered.

With respect to caloric intake, the controller can monitor usage of the enteral feeding pump to identify a quantity of calories administered to the patient. For example, the controller can determine when the estimated daily caloric intake requirement is unmet based on a comparison of the quantity of calories administered to the patient and the estimated daily caloric intake requirement. A treatment history for the patient can be generated by the controller and can include the quantity of calories delivery by the enteral feeding pump.

The enteral feeding apparatus of the present invention can also include a communication port, a computer storage, and/or an input device. The communication port can communicatively couple the apparatus to at least one device. The controller can control the communication port to receive the patient parameter and/or caloric parameter and/or can control the communication port to transmit the treatment history to a medical records database to incorporate the treatment history into an electronic medical record associated with the patient. The computer storage can receive the patient parameter and/or the caloric parameter. The controller can interface with the storage to retrieve the patient parameter and/or the caloric parameter. The input device can receive a selection from a user of the enteral feeding formula and patient information, which can be used by the controller to identify the patient parameter and the caloric parameter.

In some embodiments, the controller can identify when the estimated daily caloric intake requirement of the patient is unmet and determine a rate at which to deliver a compensatory bolus to compensate for a daily caloric intake deficit of the patient. The controller can control the enteral feeding pump to deliver the enteral feeding formula at the rate to deliver the compensatory bolus.

In another aspect, an enteral feeding system that includes an enteral feeding apparatus is disclosed. The enteral feeding system can include a pump, computer storage, and a server. The pump delivers enteral feeding formula to a patient. The computer storage stores patient information and/or formula information. The server is in communication with the enteral feeding pump and the storage. The server and/or the enteral feeding apparatus configures the enteral feeding pump to deliver the enteral feeding formula to the patient to satisfy the caloric intake requirement of the patient using a delivery parameter. The deliver parameter used to configure the pump is based on a relationship between the estimated daily caloric intake requirement and a caloric parameter included in the enteral formula information. The server and/or the enteral feeding apparatus can determine the caloric intake requirement of a patient based on patient information associated with a patient.

The server and/or the enteral feeding apparatus can identify enteral formula information associated with an enteral feeding formula selected to be administered to the patient. The caloric parameter can be a quantity of calories per a specified volume of the enteral feeding formula and/or the delivery parameter can be a delivery rate of the enteral feeding formula. The server and/or the enteral feeding apparatus can determine the delivery rate by generating a quotient of the estimated daily caloric intake requirement divided by the quantity of calories per a specified volume of feeding formula and dividing the quotient by a time period over which the enteral formula is to be delivered.

In some embodiments, the server and/or the enteral feeding apparatus can monitor usage of the pump to identify a quantity of calories administered to the patient, can determine when the estimated daily caloric intake requirement is unmet based on a comparison of the quantity of calories administered to the patient and the estimated daily caloric intake requirement, and/or can generate an enteral feeding pump treatment history for the patient that includes the quantity of calories administered.

Furthermore, the server and/or the enteral feeding apparatus can identify when a caloric intake requirement of the patient is unmet and determine a rate at which to deliver a compensatory bolus to compensate for the estimated daily caloric intake requirement of the patient that is unmet.

In yet another aspect, an enteral feeding system is disclosed that includes a computing system having at least one computing device. The computing system determines a caloric intake requirement of a patient based on patient information associated with a patient, identifies enteral formula information associated with a enteral feeding formula selected to be administered to the patient, and configures an enteral feeding pump to deliver the enteral feeding formula using a delivery parameter determined based on a relationship between the estimated caloric intake requirement and a caloric parameter included in the enteral formula information. The caloric parameter can be a quantity of calories per a specified volume of the enteral feeding formula and the delivery parameter can be a delivery rate determined by generating a quotient of the estimated daily caloric intake requirement divided by the quantity of calories per specified volume and dividing the quotient by a time period over which the enteral formula is to be delivered.

In still a further aspect, a method of administering enteral formula to a patient is disclosed. The method include determining an estimated daily caloric intake requirement for a patient based on patient information and configuring an enteral feeding pump to deliver the enteral feeding formula to satisfy the estimated daily caloric intake requirement of the patient using a delivery parameter determined based on a relationship between the estimated daily caloric intake requirement and a caloric parameter included in the enteral formula information. The method can also include administering the enteral feeding formula in response to the configuring, monitoring a quantity of calories delivered by the enteral feeding pump, and/or generating a treat history for the patient, the treatment history including the quantity of calories.

The enteral feeding pump of the present invention can be responsive to an estimated daily intake requirement so that the pump is configured to meet the feeding requirements of the patient and can be monitored to indicate when enteral feeding requirements are not being met. In this manner, embodiments of the present invention can improve patient care for enterally fed patient by ensuring patients caloric requirements are being met and that their nutritional status is not comprised. This helps prevent malnourishment, reduce health complications, and reduce length of stay in hospitals for enterally fed patients.

Additionally, embodiments of the present invention can implement compensatory bolus protocol to improve caloric intake for patients that have prolonged cessation of enteral feeding and/or who have frequent feeding interruptions in the course of the day. Using this approach, embodiments of the present invention can compensate for underfeeding of patients, which can commonly occur in hospital settings.

Any combination of the above features is envisaged. Other objects and features will become apparent from the following detailed description considered in conjunction with the accompanying drawings, wherein like reference numerals in the various drawings are utilized to designate like components. It is to be understood, however, that the drawings are designed as an illustration only and not as a definition of the limits of the invention.

BRIEF DESCRIPTION OF THE DRAWINGS

FIG. 6 an exemplary screen view for entering and viewing patient information.

FIG. 9 illustrates an exemplary treatment history.

DETAILED DESCRIPTION

Exemplary embodiments include an enteral feeding apparatus and/or system that provides computerized configuration and/or monitoring of enteral feeding to ensure proper nourishment of patients who are enterally fed. Exemplary embodiments of the enteral feeding apparatus and system can be configured to deliver enteral feeding formula to a patient based on patient information and formula information, and can monitor a patient's caloric intake to determine whether the patient is meeting the patient's caloric intake requirements. Patients that do not meet their caloric intake on a daily basis for diverse reasons (e.g., interrupted feedings, unintentional skipped feeding, held feedings for scheduled test and/or procedures) can compromise their nutritional status leading to malnutrition, increased health complications and increased length of stay in hospitals, especially in critically ill patients. Because enterally feeding patients can pose a challenge in meeting and maintaining adequate nutrition, continuous surveillance of enteral caloric intake and recognition of enteral caloric deficits is proposed.

Exemplary embodiments can include treatment histories that can include a daily caloric intake of patient, which can be used by healthcare providers to ensure that patients are receiving accurate nutrition and that caloric goals are being met for enterally fed patients. Daily monitoring of total enteral caloric intake is advantageous and can be used to prevent malnourishment when enteral feeding is frequently interrupted and/or ceased. A real time and accurate record of daily enteral caloric intake can enhance management of patient's nutritional caloric requirement.

Figure 1:
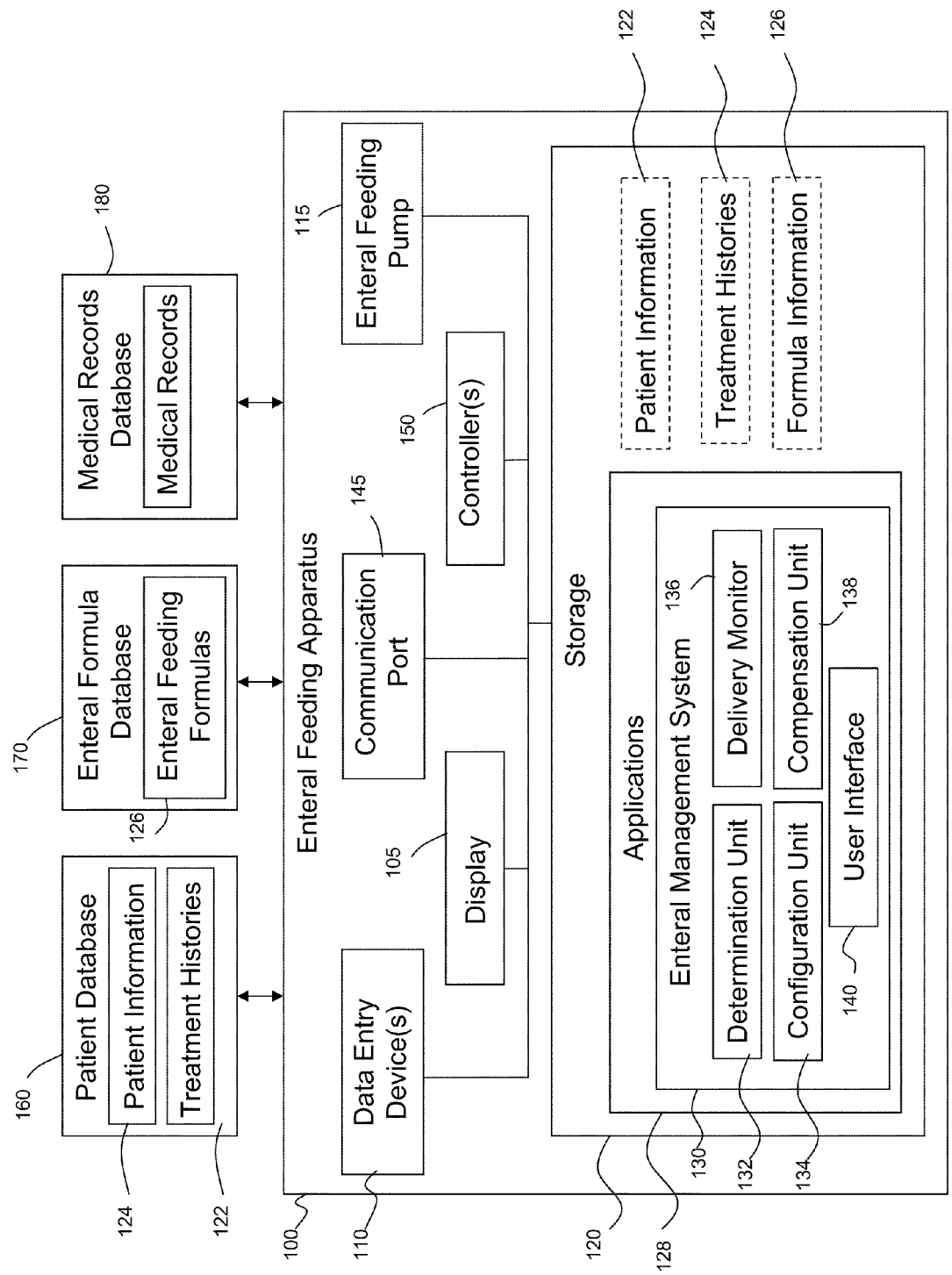
FIG. 1 is a block diagram of an exemplary enteral feeding apparatus.

FIG. 1 depicts a block diagram of an exemplary enteral feeding apparatus 100 that can include a display 105, one or more data entry devices 110, an enteral feeding pump 115

(hereinafter "pump 115"), computer storage 120, a communication port 145, and one or more processors or controllers 150 (hereinafter "controllers 150"). In some embodiments, the apparatus 100 can interface with a patient information database 160, a formula database 170, and/or a medical records database 180. The display 105 can be a liquid crystal display (LCD), plasma display, cathode ray tube (CRT) display, and the like, and can include touch screen capabilities. The one or more data entry devices 110 can include, for example, keypad, keyboard, touch screen, microphone, mouse, track ball, and the like. The pump 115 can delivery enteral formula to a patient and can be implemented using, for example, a volumetric pump with a rotary peristaltic pumping mechanism and the like.

The apparatus 100 can be used to administer enteral formula to patients that are unable to normally ingest food due to, for example, the inability to swallow, and can deliver enteral formula to a patient via an implantable or temporary enteral access device, such as a naso-gastric feeding tube (NGT), a percutaneous endoscopic gastrostomy (PEG) device, and the like, using the pump 115. Embodiments of the apparatus 100 can deliver enteral formula to a patient based on patient parameter corresponding to the patient being enterally fed and formula information corresponding to an enteral formula being delivered to a patient. The apparatus 100 can monitor its operation to ensure that the feeding requirements of the patient are being satisfied.

The storage 120 can include computer readable medium technologies, such as a floppy drive, hard drive, compact disc, tape drive, Flash drive, optical drive, read only memory (ROM), random access memory (RAM), and the like. In some embodiments, the storage 120 can store patient information 122, treatment histories 124 for patients, formula information 126, and applications 128 for operating the apparatus 100, which can include an enteral feeding management system 130. In some embodiments, the patient information 122 and treatment histories 124 can be stored in the patient database 160, treatment histories 124 can be stored in the medical records database 180, and/or the formula information 126 can be stored in the formula database 170. While the databases 160, 170, and 180 have been illustrated separately, those skilled in the art will recognize that two or more of the databases 160, 170, and 180 can be combined into a single database. The databases 160, 170, and 180 can be implemented as a relational database, a hierarchal database, and the like, and can use eXtensible Mark-up Language (XML), structured query language (SQL), and the like.

The patient information 122 is related to patients that are treated using the apparatus 100. The patient information 122 can include a patient name, patient identification number, height, weight, gender, age, allergies, as well as patient parameters, such as body mass index (BMI), body surface area (BSA), ideal body weight, adjusted body weight, an estimated daily caloric intake requirement, and the like, for each patient. Patient information 122 can be retrieved for a particular patient using, for example, a patient identifier, such as the patient's name and/or patient identification number. The patient information 122 can be sorted and/or listed by, for example, the patients name and/or patient identification number.

The patient treatment histories 124 can be stored for each patient treated using the apparatus 100. Each patient's treatment history can be associated with that patient's patient information. The treatment history 124 can include a daily enteral caloric count, a caloric goal, whether the nutritional caloric goal is met, a total amount of enteral formula fluid administered, time and duration for which the patient is enterally fed, whether and/or when compensatory boluses were delivered, and the like. In some embodiments, the caloric goal can be equal to the estimated daily caloric intake requirement of a patient.

The formula information 126 is related to enteral formulas that can be enterally delivered to a patient via the apparatus 100. The formula information 126 can include product names of enteral feeding formulas, names of manufacturers of the formulas, nutritional values of the formula including proteins, fats, carbohydrates, and electrolytes amounts (ex. potassium, magnesium, calcium, and phosphorous), as well as caloric parameters, such as a quantity of calories per a specified unit volume of the formula (e.g., calories per milliliters (cal/ml)), calories per bolus, and the like. The formula information 126 can be sorted and/or listed by, for example, product name and/or manufacturer, and can be browsed and/or searched using key words or terms.

Applications 128, such as embodiments of the system 130, can include instructions for operating the apparatus 100 upon execution by one or more of the controllers 150. The instructions can be implemented using, for example, C, C++, Java, JavaScript, Basic, Perl, Python, assembly language, machine code, and the like. The storage 120 can be local or remote to the apparatus 100. The system 130 can include an enteral feeding determination unit 132 (hereinafter "determination unit 132"), a configuration unit 134, a delivery monitor 136, a compensation unit 138, and a user interface 140.

The system 130 can be used to determine parameters for delivering enteral formula to a patient via the pump 115 and can be used to monitor or track the operation of the pump to maintain a patient treatment history, which can be used to evaluate, monitor, and determine the effectiveness of the enteral feeding treatment. In some embodiments, the system 130 can identify ineffective enteral treatment and can implement compensatory parameters for delivery of enteral formula to improve the effectiveness of the treatment. In some embodiments, the patient information 122 and the formula information 126 can be integrated into the system 130.

Using the determination unit 132, the controller 150 can calculate and/or retrieve a patient parameter to be used when configuring the pump 115. For example, the determination unit 132 can be used by the controller 150 to determine patient parameters, such as a BMI, BSA, ideal body weight, adjusted body weight, an estimated daily caloric intake requirement for a patient, and the like. Embodiments of the determination unit 132 facilitate calculation of the estimated daily caloric requirement using the patient information 122. For example, the determination unit 132 upon execution by the controller 150 can use an ideal body weight of a patient, adjusted body weight for the patient, an admission weight of the patient, the height of the patient, the gender of the patient, a body mass index (BMI) of the patient, a body surface area (BSA) of the patient, and the like, when calculating the estimated daily caloric requirement of the patient. In some embodiments, the determination unit 132 can include instructions for calculating the BMI and BSA (m2) of the patient, which can be used to calculate the estimated daily caloric intake requirement for the patient.

The controller 150 can use one or more methods of calculation provided by the determination unit 132 to estimate caloric intake requirement ($R_{kcals}$). For example, the determination unit 132 can include the Harris-Benedict equation, an Ideal body weight equation, Indirect calorimetry, Weir equation, Devine equation, a pediatric nutrition assessment calculation, and the like.

One form of Harris-Benedict equations that can be used to estimate the daily intake requirement of a patient can be expressed as follows:

Males: $R_{kcals}=66.5+13.8*W+5*H-6.8*A$

Females: $R_{kcals}=655+9.6*W+1.8*H-4.7*A$, where W is the calculation weight, which can be one of the actual weight of the patient, the admission weight, an ideal weight for the patient, an adjusted weight for the patient, and the like, expressed in kilograms, H is the height of the patient is centimeters, and A is the age of the patient in years. Another equation that can be used to estimate the daily intake requirement of a patient can be expressed as follows:

$R_{kcals}=K*W$, where K is specified number of kilocalories per kilogram per day, such as 25 to 30 kilocalories and W is the calculation weight.

One form of the ideal body weight (IBW) equations can be expressed as follows:

Males: IBW=50 kg+2.3 kg*(Height [in inches]−60)

Females: IBW=45.5 kg+2.3 kg*(Height [in inches]−60).

One form of the Devine equation can be expressed as follows:

Males: IBW=50+2.3 kg per inch over 5 feet

Females: IBW=45.5+2.3 kg per inch over 5 feet.

One form of the adjusted body weight (ABW) equations can be expressed as follows:

Males: ABW=IBW+0.4*(actual weight−IBW)

Females: ABW=0.25*(actual weight−IBW)+IBW.

The selected calculation can be dependent on a preference of a user of the apparatus 100, the unit department in which the patient is being cared, hospital policy, and the like. In some embodiments, estimation of the daily caloric intake requirement can be dependent on the nutritional state of the patient, type of patient (ex. surgical, trauma, critical and/or medical care), and the like. The determination unit 132 can also be used by the controller 150 to calculate supplemental protein and/or other nutritional supplement intake requirements for the patient. While some of the methods of calculating patient parameters including an ideal body weight, an adjusted body, and an estimated daily caloric intake requirement have been provided, those skilled in the art will recognize that other methods of calculating the patient parameters can be performed to determine the patient parameters.

Using the determination unit 132, the controller 150 can determine a delivery parameter based on a relationship between a patient parameter associated with the patient and a caloric parameter associated with the enteral feeding formula. For example, execution of the determination unit 132 by the controller 150 can facilitate determination of a delivery parameter based on a relationship between the estimated caloric intake requirement of a patient and a quantity of calories per a specified volume of enteral formula. The delivery parameter can be a delivery rate at which the pump 115 is configured to deliver enteral formula to a patient. In some embodiments, the controller 150 can determine the delivery rate by generating a quotient resulting from the estimated daily caloric intake requirement being divided by the quantity of calories per specified volume, and dividing the quotient by a time period over which the enteral formula is to be delivered. In some embodiments, the user can set the time period over which the enteral formula is to be administered. In some embodiments, a default time period can be used if one is not specified. In some embodiments, the user can set the delivery rate and the determination unit 132 can determine the time period over which the enteral formula is to be delivered to satisfy the estimated daily caloric intake requirement of the patient.

The controller 150 can execute the determination unit 132 to generate pump limit parameters to control the pump's operational range. For example, the pump limit parameters generated can include a maximum rate limit of enteral delivery, maximum rate limit for compensatory bolus, limitations on the administration of compensatory boluses, and the like. The maximum rate limit of delivery can identify the maximum amount of enteral feeding to be delivered based on the patient's caloric intake requirement and/or target rate of administration. The maximum limit for compensatory bolus delivery can identify a maximum allowable rate increase in compensating the patient's caloric deficit. The maximum limit on the administration of compensatory bolus feeds can identify the allowable administration of compensatory bolus based on patient's assessment of tolerance of the enteral feeding rate increase.

Using the configuration unit 134, the controller 150 can configure the pump 115 for delivery of the enteral feeding formula. The configuration unit 134 can be used to specify a configuration of the pump 115 for operation using the enteral formula information 126, the patient information 122, a delivery parameter, pump limit parameters, and the like. For example, the controller 150 can execute the configuration unit 134 to control delivery of the enteral formula by the pump 115 using the delivery parameter based on the relationship between a patient parameter associated with the patient and a caloric parameter associated with the enteral formula. For embodiments in which the delivery parameter is a delivery rate of the pump 115, the controller 150 can use the configuration unit 134 to configure the pump 115 to deliver the enteral feeding formula at the specified delivery rate. In this manner, the configuration unit 134 can be used to communicate with the pump 115 to set pump operation parameters so that the estimated daily caloric intake requirement calculated using the determination unit 132 can be delivered to the patient.

Upon execution of the delivery monitor 136, the controller 150 can monitor and/or track the usage of the feeding pump 115 and can store treatment information in the treatment history 124 for the patient. For example, the delivery monitor 136 can be used to maintain a log for the administration of enteral formula to a patient. The log can include formula information, patient information, and pump operation parameters used to program the apparatus 100, a volume of enteral formula administered over a specified period of time, a quantity of calories administered to the patient by the pump 115 over a specified period of time, a rate at which the pump administered the enteral formula, a start date and time of treatment sessions, an end date and time of treatment sessions, and the like. As the feeding pump 115 delivers the enteral formula, the delivery monitor 136 can be used by the controller 150 to determine the enteral calories delivered, whether the daily caloric nutritional goal is met, a caloric deficit identifying a caloric quantity that is unmet, the total volume amount of nutritional formula administered, and the like. The delivery monitor 136 can be used by the controller 150 to transmit the treatment history to the medical records database 180 for incorporation into the patient's medical record.

In some embodiments, to monitor a quantity of calories delivered to the patient, the delivery monitor 136 can be in communication with a flow sensor in the pump 115, which can monitor the flow of the formula through the feeding tube. In some embodiments, the delivery monitor can determine a quantity of calories delivered based on the delivery rate of the pump 115 and the time period over which the pump 115 has operated.

In some embodiments, the delivery monitor can turn the pump 115 off when a treatment session is completed. As one example, when the deliver monitor 136 determines that the pump has delivered the estimated daily caloric intake requirement of the patient, the deliver monitor 136 can turn the pump off. As another example, when the delivery monitor determines that the time period over which the enteral formula is to be delivered has expired, the deliver monitor can turn the pump off. Thus, the pump 115 can be controlled by the controller via execution of the delivery monitor, to stop enteral feeding based on one or more parameters.

In some embodiments, the delivery monitor can be implemented to generate one or more alarms. The alarms can indicate improper administration, operation, configuring, and the like. The alarms can provide an audible and/or visual indication to the user. For example, when the delivery monitor 136 determines that the patient is not meeting the caloric goal, the deliver monitor 136 can generate an alarm, at which point the user may choose to implement a compensatory bolus to compensate for the detected calorie deficit. While generating an alarm in response to a calories deficit is provided as an exemplary alarm condition, those skilled in the art will recognize that other alarms can be generated. For example, the delivery monitor can generate an alarm upon detecting a malfunction of the pump, when the patient is being overfed, when the delivery rate is too high or too low, and the like.

Using the compensation unit 138, the controller 150 can implement a compensatory bolus when it is determined that the estimated daily caloric intake requirement of the patient is not being met based on a comparison of a quantity of calories delivered to the patient to the estimated caloric intake requirement. The compensation unit 138 can receive a caloric deficit from the delivery monitor 136 and using the compensation unit 138, the controller 150 can calculate an amount of formula to administer to compensate for the unmet caloric intake of the patient. The compensation unit 138 can be used to provide an adjusted delivery rate to the configuration unit 134, which can be used by the controller 150 to program the pump 115 to deliver the formula at the adjusted delivery rate for a specified period of time.

In some embodiments, the compensation unit 138 can be used to implement a stepped or graduated administration rate such that the adjusted delivery rate increases and/or decrease over time. The compensatory bolus protocol can improve caloric intake for patients who are enterally fed that have prolonged cessation of enteral feeding and/or who have frequent feeding interruptions in the course of the day by compensating caloric deficits to achieve optimal daily caloric intake goal. For example, a period of time for which feeding must be stopped can be specified prior to undergoing testing and/or surgical procedures.

The user interface unit 140 can be executed by the controller 150 to provide a user interface on the display 105 to allow a user to interact with the apparatus 100. The user interface 140 can be used to allow a user to retrieve and/or display patient information 122, treatment histories 124, formula information 126, and the like, and can allow the user to enter information for use by the apparatus 100, such as patient information 122, formula information 126, and the like. For example, the user can enter patient information 122 via the user interface that can be stored and/or used when configuring the apparatus 100 and/or monitoring usage of the apparatus 100. The user interface unit 140 can be used to display usage parameters, such as a delivery rate at which the pump 150 is delivering feeding formula, a quantity of calories that have delivered within a time period, an enteral formula selected for delivery, and the like.

The communication port 145 can facilitate transmission and/or receipt of information by the apparatus 100. For example, the apparatus 100 can be communicative coupled to a communications network via the communications port 145 and the apparatus can communicate with the communications network to transmit and/or receive information over the communications network. The communication port 145 can be implemented using wired and/or wireless interfaces. For example, the communication port 145 can be configured to connect to an RJ45 cable to connect to the network and/or with an IEEE 802.11 wireless interface. The controller 150 can control the communication port 145 to transmit and/or receive information, such as patient information, formula information, selections received via the user interface, a treatment history, and the like.

Figure 2:
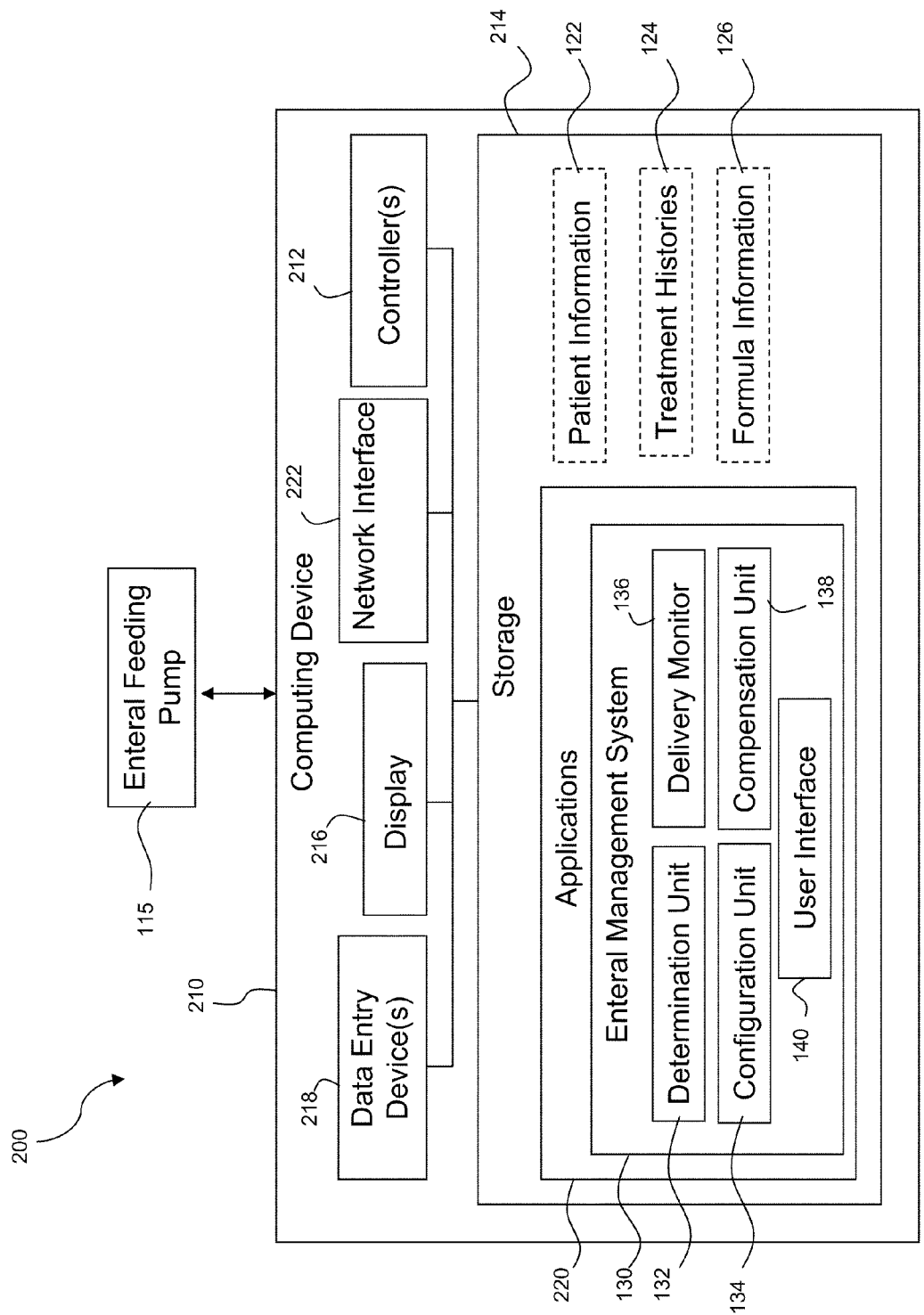
FIG. 2 is an exemplary embodiment of an enteral feeding system.

FIG. 2 is a block diagram of an exemplary enteral feeding system 200 (hereinafter "system 200") that includes a computing device 210 and the enteral feeding pump 115. The computing device 210 can be a mainframe; personal computer (PC); laptop computer; workstation; handheld device, such as a PDA and/or smart phone; and the like, and can be communicatively coupled to the pump 115. For example, the pump 115 can be a peripheral device connected to the computing device 210. In the illustrated embodiment, the computing device 210 includes one or more central processing units (CPU) or controllers 212 (hereinafter "controllers 212"), and computer storage 214. The computing device 210 can also include a display device 216. The display device 216 enables the computing device 200 to communicate with a user through a visual display. The computing device 200 can further include data entry device(s) 218, such as a keyboard, touch screen, microphone, and/or mouse. The storage 214 can include computer readable medium technologies, such as a floppy drive, hard drive, compact disc, tape drive, Flash drive, optical drive, read only memory (ROM), random access memory (RAM), and the like. The storage 214 can include the patient information 122, treatment histories 124, and formula information 126, as well as applications 220 for operation the system 200.

The applications 220, such as an embodiment of the system 130 or components thereof, can be resident in the storage 214. The storage 214 can be local or remote to the computing device 210. The computing device 210 includes network interface 222 for communicating with a communications network. The controller 212 operates to run the system 130 in storage 214 by executing instructions therein and storing data resulting from the performed instructions, which may be output via a display 216 or by other mechanisms known to those skilled in the art. The computing device 210 can communicate with the pump 115 to configure and monitor the pump 115 using the system 130.

Figure 3:
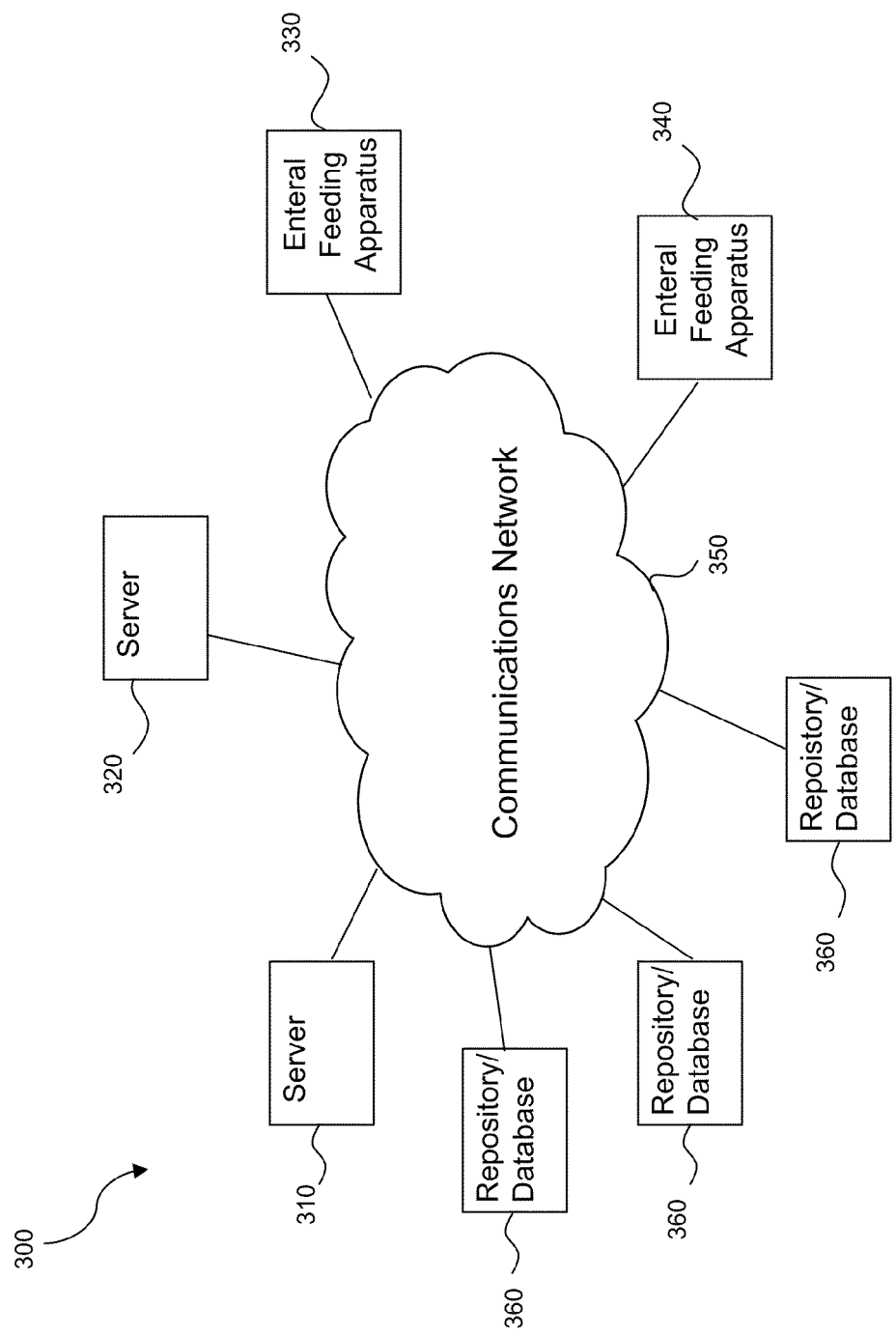
FIG. 3 is another exemplary embodiment of an enteral feeding system.

FIG. 3 depicts another exemplary enteral feeding system 300 (hereinafter "system 300"). The system 300 includes one or more servers 310 and 320 communicatively coupled to one or more enteral feeding apparatuses 330 and 340 via a communication network 250, which can be any network over which information can be transmitted between devices communicatively coupled to the network. The apparatus 330 and 340 can include one or more components of the apparatus 100 and/or the system 200. For example, in some embodiments, the apparatuses 330 and 340 can include the pump 115 and controller 150 or 212. In some embodiments, the apparatuses 330 and 340 can include the pump 115, controller 150 or 212, and the system 130 or components thereof. The system 300 can also include one or more database devices 360, which can be coupled to the servers 310/320 and apparatuses 330/340 via the communications network 350. The servers 310/320 and database devices 360 can be implemented as computing devices.

The servers 310/320, apparatuses 330/340, and/or databases 360 can store information, such as formula information, patient information, treatment histories, and the like. In some embodiments, the system 130 can be distributed among the servers 310/320, apparatuses 330/340, and/or database devices 360 such that one or more components of the system 130 and/or a portion of one or more components of the system 130 can be implemented by a different device (e.g. servers, pumps, databases) in the enteral feeding system 300. For example, the determination unit 132 can be resident on the servers 310 and 320; the configuration unit 134, the delivery monitor 136, and compensation unit 138 can be resident on the apparatuses 330 and 340; and the patient information 122 and formula information 126 can be stored in one or more of the database devices 360.

Figure 4:
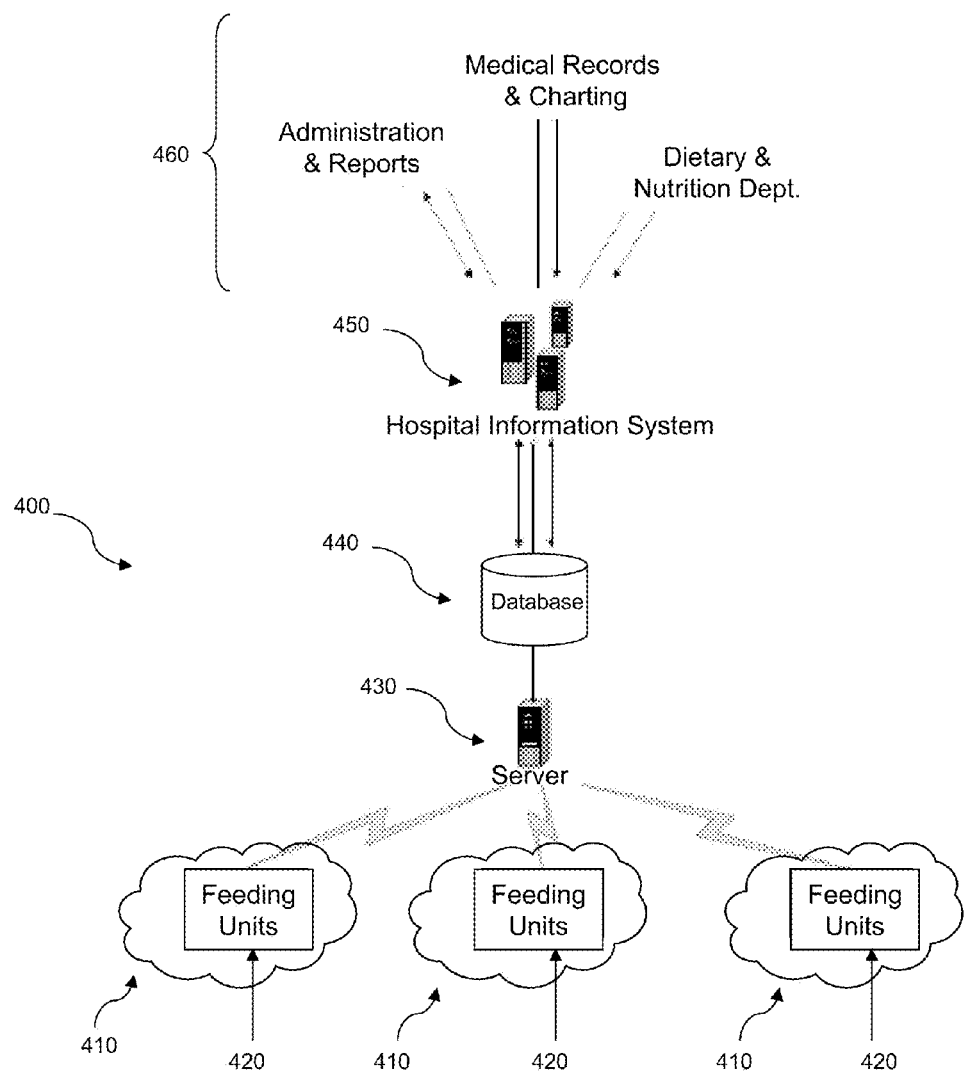
FIG. 4 is an exemplary implementation of embodiments of an enteral feeding apparatus and/or system in a hospital environment.

FIG. 4 is an exemplary hospital environment 400 in which embodiments of the apparatus 100, system 200, and/or system 300 can be implemented. The hospital environment 400 can include hospital treatment units 410 in which patients may require enteral feeding. Each of the units 410 can include embodiments of one or more of the apparatus 100, system 200, and or apparatus 330 (hereinafter collectively referred to as "feeding units 420"). In some embodiments, the feeding units 420 can be connected to a server 430, which can be in communication with a database device 440. Each feeding unit 420 can connect to the network via a RJ45 cable and/or a wireless interface. Information, such as formula information and/or patient information input to the feeding units 420 by a user can be transferred to the sever 430, which can store the information in the database device 440. The database 440 can be in communication with a hospital information system network 450 to facilitate access to the database 440 by hospital departments 460. In this manner, information in the database 440 can be distributed to the hospital departments 460, which can include a dietary and nutrition department, an administration and reports department, a medical records and charting department, and the like.

Figure 5:
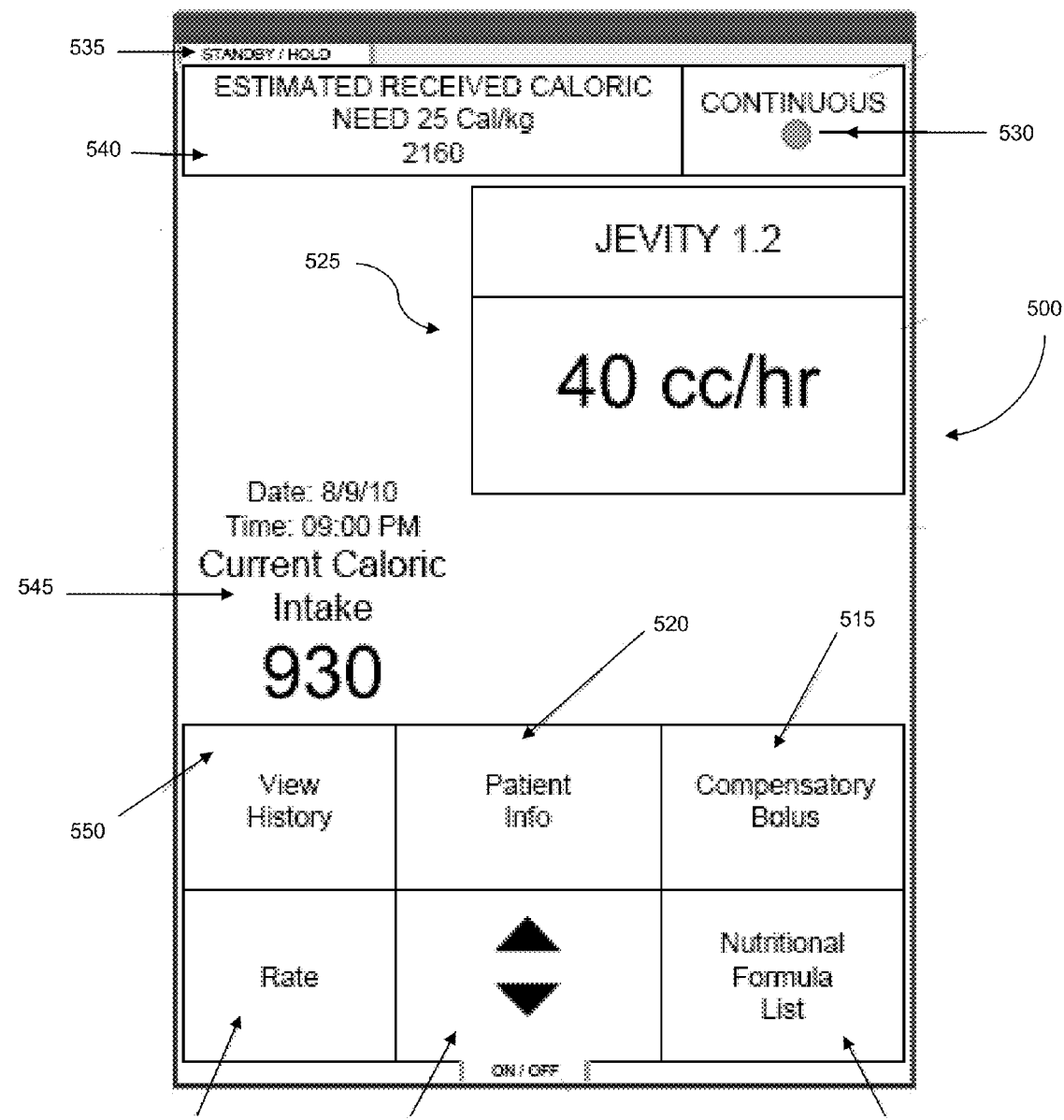
FIG. 5 illustrates an exemplary screen view to facilitate user interaction with embodiments of an enteral feeding apparatus and/or system.

FIG. 5 is an exemplary illustration of an embodiment of a main view screen 500 of a user interface displayed by embodiments of the apparatus 100, system 200, and system 300 (hereinafter collectively referred to as "feeding embodiments 502"). The view screen 500 can display information including formula information, patient information, pump operation parameters, treatment history information, and the like. For example, the view screen 500 can display patient specific information to a user and can allow the user to input information by touching defined areas in the screen, which can be used to interface with components of the feeding embodiments 502 including, for example, the patient information 122, the treatment histories 124, the formula information 126, components of the system 130, the pump 115, and the like.

The defined area 510 can be selected to display an enteral formula list using the formula information 126. The list can include each individual enteral formula product name, nutrient value, calories, calories per milliliter, and the like. The user can select the defined area 510 to browse through the available formulas to be used when configuring the feeding embodiments 502 for operation. When the user identifies an enteral formula to be used, the user can select the enteral formula from the list. In some embodiments, a data entry field can be displayed upon selecting the defined area 510 to permit searches for enteral formulas using key words or terms. If the user is unable to find the formula in the list, the user can enter formula information manually and the entered formula information can be stored.

The defined area 515 can be selected to access the deliver monitor 136 and/or the compensation unit 138. Upon selection of the defined area 515, the feeding embodiments 502 can display a compensatory bolus feeding view to identify a calorie deficit for a patient based on the estimated daily caloric requirement of the patient and the quantity of calories delivered to the patient. The usage information stored by delivery monitor 136 of the feeding embodiments 502 can provide a current nutritional status of the patient and facilitate compensation of caloric deficits using compensatory bolus feeding.

The defined area 520 can be selected to display patient information input by the user and/or retrieved from the patient information. For example, upon selection of the defined area 520, the user can input the patient's height, weight, age, gender, and the like, into data entry fields and/or can retrieve patient information using a key word or term search. For example, selection of the defined area 520 can prompt the user for a patient identifier number and can retrieve the patient information that corresponds to the patient identification number entered by the user. Upon entry or selection of patient information, the feeding embodiments 502 can use the patient information for controlling the delivery of enteral formula. For example, once the patient information is identified, the determination unit can be used to determine patient parameters including the BMI, BSA, and estimated daily caloric intake requirement of the patient, which can be displayed in defined area 540.

The defined area 525 can display a delivery rate at which the pump of the feeding embodiments is programmed to deliver the enteral formula. The delivery rate can be determined by the feeding embodiments 502 when the enteral formula and patient information are identified. The defined area 525 can also display the name of the enteral formula being delivered to the patient, with its caloric value, shown in the present example as calories per milliliter (cal/ml).

The defined area 530 can display a blinking LED light that can be viewed to ensure that the pump is functioning and administrating the enteral formula in accordance with the configuration of the feeding embodiments 502. The defined area 530 can include an indicator to display the type of administration of the enteral feeding being delivered, such as a continuous, intermitted, bolus feeding, and the like.

The defined area 535 can be selected to change the operational state of the pump to a standby/hold state. The defined area 535 allows a user to stop the pump for procedures, intermittent disconnection from the enteral pump, and the like. When the user wishes to resume enteral feeding, the user can select the defined area 535 and enteral feeding can restart.

The defined area 545 can provide a real-time display of the date and time. The feeding embodiments 502 can use the date and time to track and control the actual time and day the administration of enteral formula was delivered. The advantage of having a real-time clock gives the user the ability to accurately monitor the actual caloric intake the patient receives on a daily basis. This can facilitate accurate compensation of enteral feeding when a caloric deficit is evident and visible in the feeding embodiments 502.

The defined area 550 can be selected to display a history view screen that stores patient specific treatment histories. The history view screen can be accessed to retrieve and/or view a daily caloric intake goal, whether the caloric intake goal is being met, a caloric deficit based on a comparison of calories delivered to the patient and the calorie intake goal, and the like. The history view screen can provide a precise and accurate nutritional status of the patient.

The defined area 560 can be used to control various parameters of the feeding embodiments 502. For example, the defined area 560 can be used to manually increase and/or decrease the delivery rate, which can provide an override function to override the rate set by the feeding embodiments 502. In some embodiments, the user may require special authorization prior to overriding the delivery rate specified by the feeding embodiments 502.

FIG. 6 is an exemplary screen 600 that can be displayed upon selection of the defined area 520 (FIG. 5). The user can begin by entering patient information for a patient in data entry fields 610, such as patient gender, height, admission weight, the hospital unit department, and/or the amount of kcal/kg to be used. In some embodiments, the data entry fields can be pre-populated in response to receiving a patient identifier, such as the patient's name and/or patient identification number. Once the patient information is entered and/or retrieved, the determination unit can calculate the BMI and BSA of the patient.

Upon selection of the calculate caloric intake requirement button 615, and the determination unit can determine the ideal body weight of the patient, the adjusted body weight for the patient, and/or a weight used for the caloric intake requirement calculation, which can be the admission weight, ideal body weight, or the adjusted body weight. The determination unit can also calculate the estimated daily caloric intake requirement for the patient. These patient parameters can be displayed in area 620. In some embodiments, the feeding embodiments can be programmed by particular units/departments in a hospital (for ex. a particular unit may use an automatic set number of kcal/kg for the common patient in that specific unit) to have a default estimated daily caloric intake requirement of 25-30 kcal/kg. In some embodiments, the default value can be modified by the user.

In some embodiment, the determination unit can be programmed to use the adjusted body weight when calculating the estimated daily caloric requirement for patients with a BMI >30. In some embodiments, the adjusted body weight can be calculated using the Devine equation. The determination unit can include different methods of calculating the daily caloric intake requirements. In some embodiments, a selection of a method of calculating the estimated daily caloric intake requirements can be dependent on the user's preference, unit department, and/or hospital policy. Once the estimated daily caloric intake requirement is calculated, a table 625 of the enteral formulas can be displayed. The names of the enteral formulas can listed in a column 630 along with the calories per volume of the enteral formula. The column 632 can include and estimated delivery rate at which the formula would be delivered to reach the estimated caloric intake requirement. The column 634 can include an estimated quantity of total calories to be delivered in a day at the corresponding delivery rate. The column 636 can include a quantity of protein that would be delivered in the day for each enteral formula listed. Those skilled in the art will recognize that other nutritional values can be included in the table and monitored by the feeding units.

Figure 7:
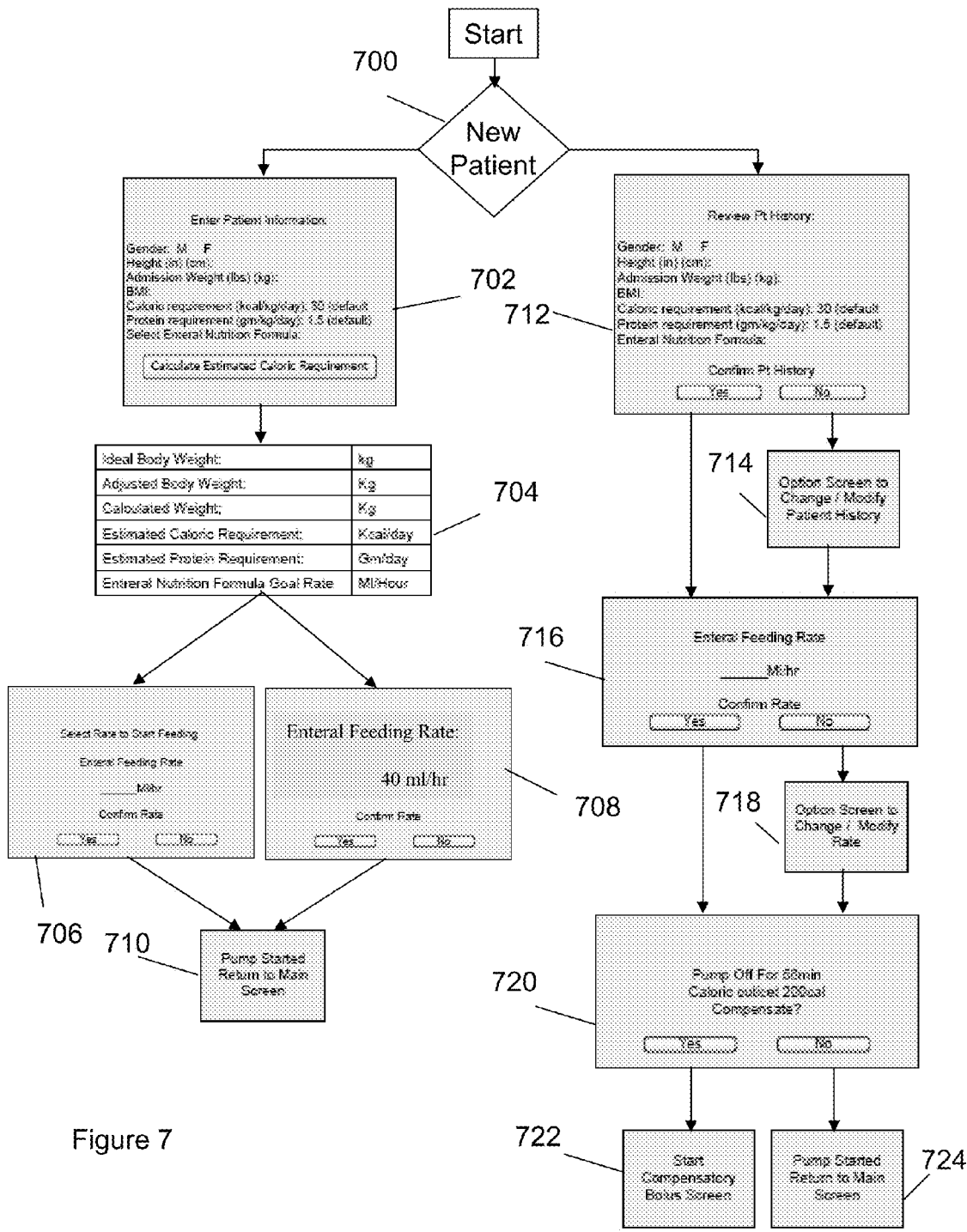
FIG. 7 illustrates entering patient information for use in determining patient parameters.

FIG. 7 illustrates a process for entering information via the user interface. A user can select whether this is a new patient (700). If the patient is a new patient (702), a screen is displayed to the user in which the user inputs the patient information and prescribed enteral formula (704) and patient parameters are calculated and displayed (706). The patient parameters can include, for example, the estimated caloric requirement, protein requirement, ideal and adjusted body weight, calculated weight, an enteral formula delivery rate for the patient, and the like. In some embodiments, the feeding embodiments can set the delivery rate based on, for example a time period of which the enteral formula is to be delivered and prompt the user to confirm (708). In some embodiments, the user is prompted to enter a desired delivery rate and can confirm the delivery rate and the time period over which the formula to be delivered is determined by the determination unit (710). After the delivery rate is specified, the user can start the pump and the user interface returns to the main view screen (712).

If the patient is not a new patient (702), a review history screen menu can be displayed with patient information and formula information corresponding to the last patient to use the feeding embodiments (714). The user is prompted to review and verify the patient's information and confirm that it is correct. If the information is not accurate, the user has the option to change and modify the information (716). Once the appropriate information is established, the user can confirm the recalled delivery rate (718) and/or the user may also have the option change and modify the rate if needed (720). Once the appropriate rate is selected, the feeding embodiments have the capability to calculate the duration of time the pump was off, and therefore, the feeding embodiments can accurately calculate the caloric deficit of the patient. For example, the user then has the option to compensate and replace the calories that the patient did not receive when the pump was turn off (722). If the user selects to compensate the patient's calories, the option screen to compensate the patient's caloric deficit is displayed (724). Otherwise, the pump starts delivery enteral formula at the confirmed delivery rate (726).

Figure 8:
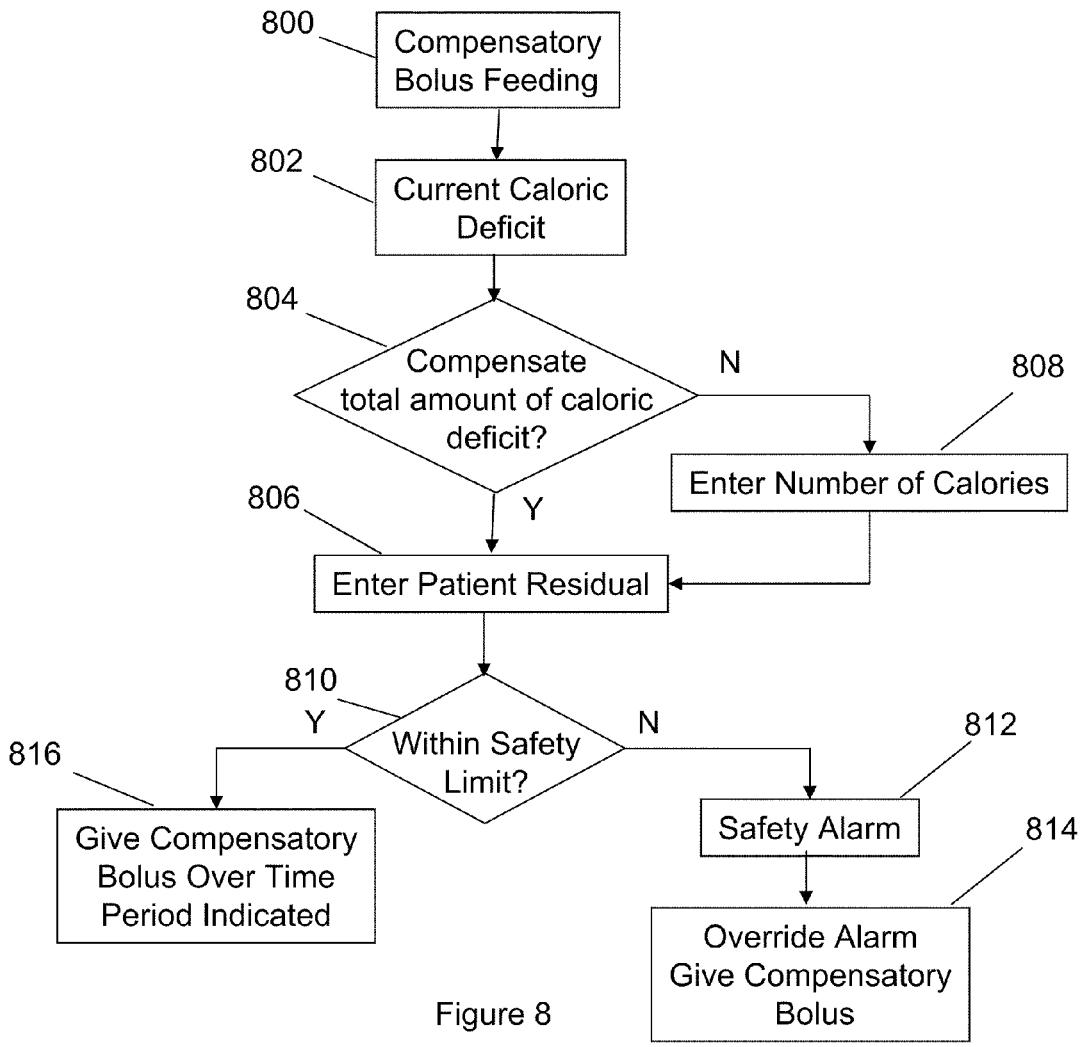
FIG. 8 illustrates programming a particular enteral feeding protocol to deliver a compensatory bolus.

FIG. 8 illustrates programming a particular enteral feeding protocol for delivery a compensatory bolus. The compensatory bolus feeding protocol is a feature that allows accurate calculation of the patient's total caloric deficit based on the time the enteral feeding was held, interrupted, and/or turned off. The compensatory bolus feature is not limited to compensating caloric deficit and can compensate a patient if the user anticipates the patient's enteral feeding is to be interrupted in the future. Once the user proceeds to select the compensatory bolus (800), the feeding embodiments can determine the total caloric deficit of the patient (802). The user can be prompted to indicate whether the total caloric deficit is to be compensated (804).

If the total amount of caloric deficiency is desired to be compensated, the user can enter the residual volume of enteral formula remaining prior to administration of bolus feeding (806). If the user does not desire to administer the total amount of caloric deficit, the user may input the desired volume and/or calories (808) followed by entering the patient's residual volume (806). In some embodiments, the compensation unit of the feeding embodiments can include a safety feature that allows the user to assess the patient's tolerance of compensatory bolus feeding prior to administration. The patient's residual volume is input by the user.

The safety parameters can be applied for the compensatory bolus protocol to limit the amount of residual volume prior to be administered using a compensatory bolus feed (810). For example, if the safety parameter is not satisfied (e.g., if the residual volume is >250 ml), an alarm can be generated indicating that the safety parameter is not satisfied (e.g., the residual volume is too high) (812). In some embodiments, the safety limit may be a hard limit that cannot be overridden, and therefore the bolus cannot be administered. In some embodiments, the safety limit can be a soft limit that can be overridden and the user can override the alarm to facilitate delivery of the compensatory bolus (814). If the residual volume is less than the safety limit parameter (810), the user can administer the compensatory bolus and the length of time the compensatory bolus will run to achieve total caloric compensation is displayed (816). The enteral feeding pump unit may be programmed to deliver the compensatory bolus feed by automatically increasing the rate over a period of time for example, increasing the target rate by 50%, over 6 hours. The rate increase parameter can be programmed by the user for particular patients and/or location in the hospital.

FIG. 9 is an exemplary patient treatment history 900. The treatment history can include a date and time entry 902, the enteral formula administered 904, the delivery rate 906 at which the enteral formula was delivered, a total enteral feeding volume administered in the last 24 hours 908, and a total quantity of calories administered in the last 24 hours 910 for each treatment session.

The history data can also include an estimated caloric intake requirement for each session 912 and a 24 hours total caloric deficit of the patient 914 for each treatment session. The treatment history 900 can also indicate a quantity of calories delivered to the patient via a compensatory bolus 916 for each session. The treatment history 900 can interface with and/or be incorporated into the electronic medical record of the patient, and can be included in an intake and output flowsheet as well as a nutrition flowsheet. The treatment history 900 can be used to calculate a cumulative amount of the patient's total caloric intake, and/or the percentage of the caloric goal met.

While exemplary embodiments have been described herein, it is expressly noted that the present invention is not limited to these embodiments, but rather the intention is that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

The invention claimed is:

1. An enteral feeding apparatus comprising:
an enteral feeding pump to deliver enteral feeding formula to a patient; and
a controller configured to control delivery of the enteral feeding formula based on a delivery parameter determined using a relationship between a patient parameter associated with the patient and a caloric parameter associated with the enteral feeding formula; wherein the delivery parameter is a delivery rate of the enteral feeding formula; wherein the delivery rate is determined by generating a quotient of the estimated daily caloric intake requirement divided by the quantity of calories per specified volume and dividing the quotient by a time period over which the enteral formula is to be delivered.

2. The apparatus of claim 1, wherein the patient parameter is an estimated daily caloric intake requirement for the patient.

3. The apparatus of claim 2, wherein the controller calculates the daily estimated caloric intake requirement for the patient based on patient information associated with the patient.

4. The apparatus of claim 3, wherein the estimated daily caloric intake requirement is calculated using at least one of the Weir equation, the indirect calorimetry respiratory quotient formula, Harris Benedict equation, the ideal bodyweight equation, the Devine formula equation, and the adjusted body weight equation.

5. The apparatus of claim 2, wherein the caloric parameter is a quantity of calories per a specified volume of the enteral feeding formula.

6. The apparatus of claim 2, wherein the controller monitors usage of the enteral feeding pump to identify a quantity of calories administered to the patient.

7. The apparatus of claim 6, wherein the controller determines when the estimated daily caloric intake requirement is unmet based on a comparison of the quantity of calories administered to the patient and the estimated daily caloric intake requirement.

8. The apparatus of claim 6, wherein the controller generates a treatment history for the patient that includes the quantity of calories delivery by the enteral feeding pump.

9. The apparatus of claim 8, further comprising:
a communication port to communicatively couple the apparatus to at least one device, the controller controlling the communication port to transmit the treatment history to a medical records database to incorporate the treatment history into an electronic medical record associated with the patient.

10. The apparatus of claim 2, wherein the controller identifies when the estimated daily caloric intake requirement of the patient is unmet and determines a rate at which to deliver a compensatory bolus to compensate for the estimated daily caloric intake requirement of the patient that is unmet.

11. The apparatus of claim 10, wherein the controller controls the enteral feeding pump to deliver the enteral feeding formula at the rate.

12. The apparatus of claim 1, further comprising: storage to receive at least one of the patient parameter and the caloric parameter, the controller being configured to interface with the storage to retrieve the at least one of the patient parameter and the caloric parameter.

13. The apparatus of claim 1, further comprising: a communication port to communicatively couple the apparatus to at least one device, the controller controlling the communication port to receive at least one of the patient parameter and the caloric parameter.

14. The apparatus of claim 1, further comprising: an input device to receive a selection from a user of the enteral feeding formula and patient information, the patient parameter and the caloric parameter being identified in response to the selection.

15. A enteral feeding system comprising:
an enteral feeding apparatus including a pump to deliver enteral feeding formula to a patient;
a storage to store at least one of patient information and formula information; and
a server in communication with the enteral feeding pump and the storage, wherein at least one of the server and the enteral feeding apparatus configures the enteral feeding pump to deliver the enteral feeding formula to satisfy the caloric intake requirement of the patient using a delivery parameter based on a relationship between the estimated daily caloric intake requirement and a caloric parameter included in the enteral formula information; wherein the caloric parameter is a quantity of calories per a specified volume of the enteral feeding formula and the delivery parameter is a delivery rate of the enteral feeding formula; wherein at least one of the server and the enteral feeding apparatus determines the delivery rate by generating a quotient of the estimated daily caloric intake requirement divided by the quantity of calories per a specified volume of feeding formula and dividing the quotient by a time period over which the enteral formula is to be delivered.

16. The system of claim 15, wherein at least one of the server and the enteral feeding apparatus determines the caloric intake requirement of a patient based on patient information associated with a patient.

17. The system of claim 15, wherein at least one of the server and the enteral feeding apparatus identify enteral formula information associated with a enteral feeding formula selected to be administered to the patient.

18. The system of claim 15, wherein at least one of the server and the enteral feeding apparatus monitors usage of the pump to identify a quantity of calories administered to the patient.

19. The system of claim 18, wherein at least one of the server and the enteral feeding apparatus determines when the estimated daily caloric intake requirement is unmet based on a comparison of the quantity of calories administered to the patient and the estimated daily caloric intake requirement.

20. The system of claim 18, wherein at least one of the server and the enteral feeding apparatus generates an enteral feeding pump treatment history for the patient that includes the quantity of calories administered.

21. The system of claim 15, wherein at least one of the server and the enteral feeding apparatus identifies when a caloric intake requirement of the patient is unmet and determines a rate at which to deliver a compensatory bolus to compensate for the estimated daily caloric intake requirement of the patient that is unmet.

22. The system of claim 15, wherein the enteral feeding apparatus includes an input device to receive a selection from a user of the enteral feeding formula and patient information, the estimated daily caloric requirement and the caloric parameter being determined in response to the selection.

23. An enteral feeding system comprising:
a computing system including at least one computing device, the computing system being configured to:
determine a caloric intake requirement of a patient based on patient information associated with a patient;
identify enteral formula information associated with a enteral feeding formula selected to be administered to the patient; and configure an enteral feeding pump to deliver the enteral feeding formula using a delivery parameter determined based on a relationship between the estimated caloric intake requirement and a caloric parameter included in the enteral formula information; wherein the caloric parameter is a quantity of calories per a specified volume of the enteral feeding formula and the delivery parameter is a delivery rate determined by generating a quotient of the estimated daily caloric intake requirement divided by the quantity of calories per specified volume and dividing the quotient by a time period over which the enteral formula is to be delivered.

24. A method of administering enteral formula to a patient comprising:
determining an estimated daily caloric intake requirement for a patient based on patient information; configuring an enteral feeding pump to deliver the enteral feeding formula to satisfy the estimated daily caloric intake requirement of the patient using a delivery parameter determined based on a relationship between the estimated daily caloric intake requirement and a caloric parameter included in the enteral formula information; wherein the delivery parameter is a delivery rate of the enteral feeding formula; wherein the delivery rate is determined by generating a quotient of the estimated daily caloric intake requirement divided by the quantity of calories per specified volume and dividing the quotient by a time period over which the enteral formula is to be delivered.

25. The method of claim 24, further comprising: administering the enteral feeding formula in response to the configuring.

26. The method of claim 24, further comprising: monitoring a quantity of calories delivered by the enteral feeding pump.

27. The method of claim 24, further comprising: generating a treat history for the patient, the treatment history including the quantity of calories.

* * * * *